(12) United States Patent
Xi

(10) Patent No.: US 8,033,999 B2
(45) Date of Patent: Oct. 11, 2011

(54) SYSTEM AND METHOD FOR MONITORING MYOCARDIAL INSTABILITY

(75) Inventor: Cecilia Qin Xi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 384 days.

(21) Appl. No.: 12/340,370

(22) Filed: Dec. 19, 2008

(65) Prior Publication Data

US 2010/0160800 A1    Jun. 24, 2010

(51) Int. Cl.
*A61B 5/02* (2006.01)
*A61B 5/04* (2006.01)

(52) U.S. Cl. ........................................ 600/508; 600/509

(58) Field of Classification Search ........... 600/508–523
See application file for complete search history.

(56) References Cited

U.S. PATENT DOCUMENTS

| | | | |
|---|---|---|---|
| 6,308,094 B1 * | 10/2001 | Shusterman et al. | 600/516 |
| 6,459,928 B2 * | 10/2002 | Mika et al. | 600/510 |
| 7,127,290 B2 | 10/2006 | Girouard et al. | |
| 7,308,308 B1 * | 12/2007 | Xi et al. | 607/14 |
| 7,634,309 B2 * | 12/2009 | Wariar et al. | 600/514 |
| 7,801,591 B1 * | 9/2010 | Shusterman | 600/509 |
| 7,865,232 B1 * | 1/2011 | Krishnaswamy et al. | 600/509 |
| 2004/0220632 A1 | 11/2004 | Burnes | |

FOREIGN PATENT DOCUMENTS

| | | |
|---|---|---|
| WO | 2004012815 | 2/2004 |
| WO | 2004101062 | 11/2004 |

\* cited by examiner

*Primary Examiner* — Niketa Patel
*Assistant Examiner* — Catherine Voorhees
(74) *Attorney, Agent, or Firm* — Theresa Takeuchi; Steven M. Mitchell

(57) ABSTRACT

A method of monitoring myocardial stability includes determining a window length representing an acceptable time period between potential start times associated with at least two physiologic indices and monitoring multiple physiologic indices representative of myocardial stability. Predetermined variations in each of the physiologic indices denote the potential start times and potential end times for candidate events that are indicative of myocardial instability. The method further includes identifying the potential start times associated with at least two of the physiologic indices and declaring at least one of the candidate events to be an actual event of myocardial instability based on the window length and a time period between the potential start times identified by the identifying operation.

25 Claims, 9 Drawing Sheets

SYSTEM AND METHOD FOR MONITORING MYOCARDIAL INSTABILITY

FIELD OF THE INVENTION

Embodiments of the present invention pertain generally to implantable and external medical devices, and more particularly pertain to methods and systems that monitor myocardial instability.

BACKGROUND OF THE INVENTION

Myocardial instability such as atrial and/or ventricular fibrillation, tachycardia, bradycardia, myocardial infarction, and the like, may pose significant health risks to patients. For example, pulmonary edema may lead to respiratory failure of patients. Ventricular arrhythmia such as ventricular fibrillation may lead to cardiac arrest and death. One or more physiological parameters of the patients related to cardiac function may be tracked in order to treat the patient and thus reduce the likelihood of sudden cardiac arrest and death.

For example, congestive heart failure (CHF) is an imbalance in pump function in which the heart fails to maintain appropriate blood circulation. The most severe manifestation of CHF, cardiogenic pulmonary edema (PE), develops when this imbalance causes a patient's heart to have difficulty clearing or moving fluid through or from the left ventricle out of the heart. The fluid may back up through the patient's circulatory system and accumulate in the patient's lungs. The amount of fluid that is accumulated in the lung may be one indicator of cardiogenic pulmonary edema. Changes in electrical impedance across the heart and lung may be tracked in order to determine the severity of the myocardial instability, as well as to track the onset and termination of events or episodes of heart failure. These changes in electrical impedance represent one physiological parameter of a variety of physiological parameters that may be used to track episodes of myocardial instability. Conventional systems exist that monitor sets of physiologic parameters and identify myocardial instability when the physiologic parameters change by predetermined amounts.

However, conventional systems have experienced disadvantages when monitoring physiological parameters for the purpose of tracking the occurrence and frequency of episodes of myocardial instability. For example, in known systems where too few parameters may be monitored, a change in one parameter may incorrectly be associated with an episode of myocardial instability when in fact the parameter change is due to something else. Moreover, the parameters that are monitored may be dependent on one another. For example, an increase in the measured value of a first parameter may result in a related increase in the measured value of a second parameter. When both of the first and second parameters are tracked to determine the onset of an episode of myocardial instability, then an increase in the first parameter, that is unrelated to myocardial instability, may result in a corresponding increase in the second parameter to be attributed to myocardial instability. As a result, when a relatively small number of parameters are monitored and/or the monitored parameters are dependent on one another, the number of falsely detected episodes of myocardial instability, or "false positives," may be undesirably high.

Thus, a need exists to improve the accuracy of methods and systems that track the occurrence of events of myocardial instability and to decrease the number of false positive as detected events of myocardial instability.

BRIEF SUMMARY OF THE INVENTION

In one embodiment, a method of monitoring myocardial stability is provided. The method includes determining a window length representing an acceptable time period between potential start times associated with at least two physiologic indices and monitoring multiple physiologic indices representative of myocardial stability. Predetermined variations in each of the physiologic indices denote the potential start times and potential end times for candidate events that are indicative of myocardial instability. The method further includes identifying the potential start times associated with at least two of the physiologic indices and declaring at least one of the candidate events to be an actual event of myocardial instability based on the window length and a time period between the potential start times identified by the identifying operation. The physiologic indices may be uncorrelated with respect to one another. Optionally, the method also includes identifying a known prior event of myocardial instability and known start times for multiple physiologic indices corresponding to the known prior event and deriving the window length based on a time period between the known start times corresponding to the known prior event.

In another embodiment, a computer readable storage medium for a computing device having a memory and a microcontroller is provided. The computer readable storage medium includes instructions to direct the memory to store values of multiple physiologic indices indicative of myocardial stability. The computer readable storage medium also includes instructions to direct the microcontroller to determine a window length representing an acceptable time period between potential start times associated with at least two of the physiologic indices and monitor multiple physiologic indices. Predetermined variations in each of the physiologic indices denote the potential start times and potential end times for candidate events indicative of myocardial instability. The instructions also direct the microcontroller to identify the potential start times associated with at least two of the physiologic indices and declare at least one of the candidate events to be an actual event of myocardial instability based on the window length and a time period between the identified potential start times. The physiologic indices may be uncorrelated with respect to one another. Alternatively, the instructions direct the memory to store values of multiple physiologic indices indicative of myocardial stability for each of multiple patients. The instructions also direct the microcontroller to identify, for each patient, a known prior event and known start times for the multiple physiologic indices corresponding to the known prior event and derive the window length based on a time period between the known start times for the multiple patients.

In another embodiment, a system for monitoring myocardial stability includes sensors and a computing device. The sensors are configured to obtain values of multiple physiologic indices representative of myocardial stability. The computing device is configured to examine the physiologic indices to determine whether predetermined variations in the physiologic indices represent myocardial instability. The computing device determines whether the predetermined variations represent myocardial instability by determining a window length indicative of an acceptable time period between potential start times associated with at least two physiologic indices and by monitoring multiple physiologic indices for predetermined variations. The predetermined variations are indicative of the potential start times and potential end times for candidate events representative of myocardial instability. The computing device also identifies the potential start times associated with at least two of the physiologic indices and declares at least one of the candidate events to be an actual event of myocardial instability based on the window length and a time period between the potential start times identified by the identifying operation. The physiologic indices may be uncorrelated with respect to one another. Optionally, the computing device is configured to identify the potential end times associated with at least two of the physiologic indices and determine an event end time at which the actual event terminates based on the potential end times identified by the computing device.

BRIEF DESCRIPTION OF THE DRAWINGS

The drawings, which are not necessarily drawn to scale, illustrate generally, by way of example, but not by way of limitation, various embodiments discussed in the present document.

DETAILED DESCRIPTION OF THE INVENTION

In the following detailed description, reference is made to the accompanying drawings which form a part hereof, and in which are shown by way of illustration specific embodiments in which the present invention may be practiced. These embodiments, which are also referred to herein as "examples," are described in sufficient detail to enable those skilled in the art to practice the invention. It is to be understood that the embodiments may be combined or that other embodiments may be utilized, and that structural, logical, and electrical variations may be made without departing from the scope of the present invention. For example, embodiments may be used with a pacemaker, a cardioverter, a defibrillator, and the like. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

In accordance with certain embodiments, methods and systems are provided that are able to monitor variations or excursions in multiple physiologic indices that are indicative of myocardial stability. The physiologic indices that are monitored may be representative of the same type of myocardial instability. The variations are monitored for several patients in order to determine which of the variations in the indices represent actual events of myocardial instability. The monitoring of the variations in the physiologic indices may aid in reducing the number of misdiagnosed or undiagnosed episodes of myocardial instability. For example, multiple physiological indices may be monitored to confirm when an increase in one or more of the indices is related to or associated with myocardial instability.

Figure 1:
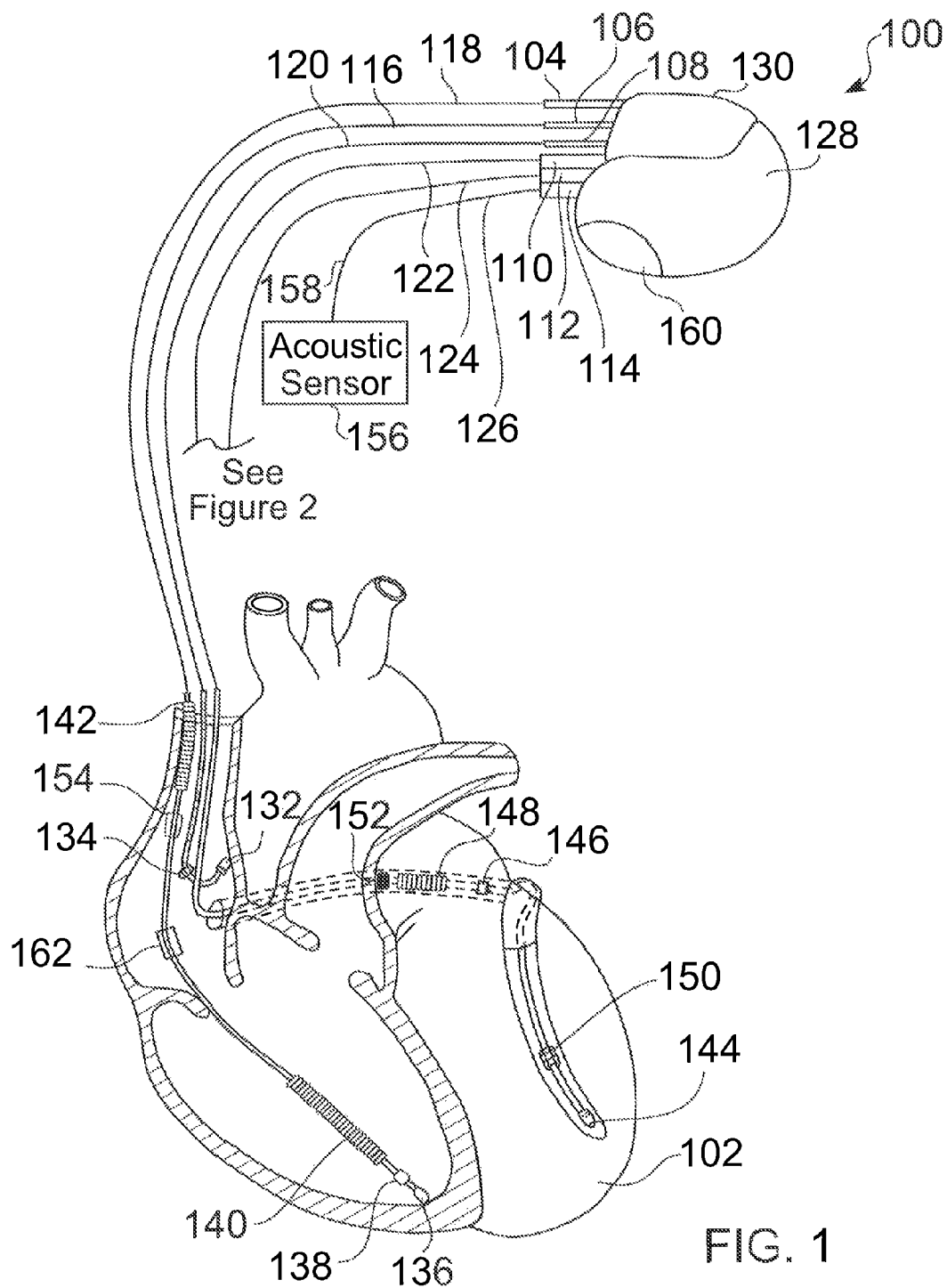
FIG. 1 illustrates an IMD that is implemented in accordance with one embodiment.

FIG. 1 illustrates an IMD 100 that is formed in accordance with an embodiment of the present invention and that is coupled to a heart 102. The IMD 100 may be a cardiac pacemaker, an ICD, a cardiac resynchronization therapy (CRT) pacemaker, a cardiac resynchronization therapy defibrillator (CRT-D), and the like, implemented in accordance with one embodiment of the present invention. The IMD 100 may be a triple- or quad-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. Optionally, the IMD 100 may be a multisite stimulation device capable of applying stimulation pulses to multiple sites within each of one or more chambers of the heart 102.

Figure 2:
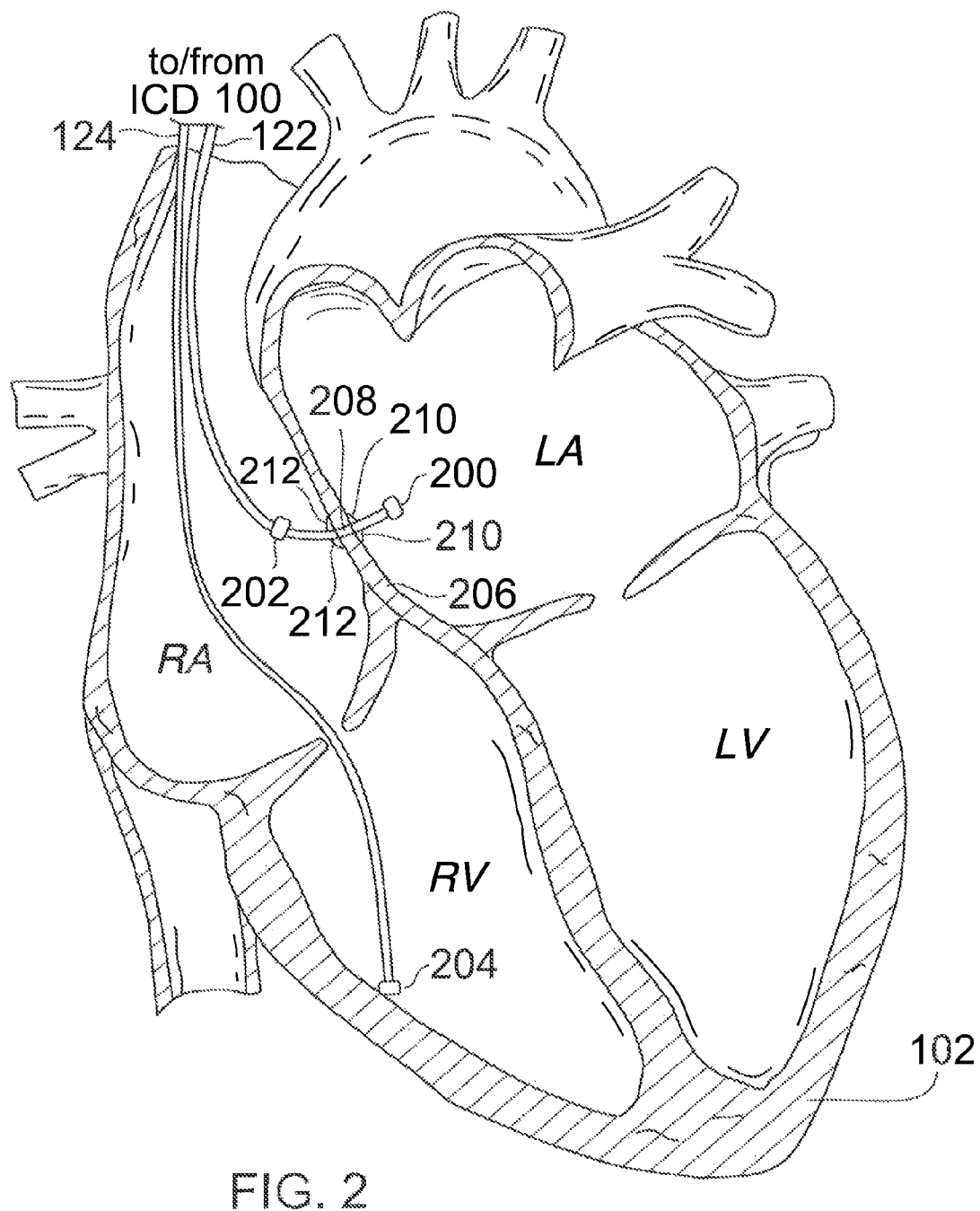
FIG. 2 illustrates a distal portion of pressure leads shown in FIG. 1.

The IMD 100 includes a housing 128 that is joined to a header assembly 130 that holds receptacle connectors 104-114. The receptacle connectors 104-114 are connected to various leads, such as a right atrial lead 116, a right ventricular lead 118, and a coronary sinus lead 120. One or more of the leads 116, 118, 120 detect intracardiac electrogram (IEGM) signals that form an electrical activity indicator of myocardial function over multiple cardiac cycles. The IEGM signals represent analog signals that are subsequently digitized and analyzed to identify waveforms of interest. Examples of waveforms identified from the IEGM signals include the P-wave, T-wave, the R-wave, the QRS complex and the like. The IMD 100 also may be connected by the receptacle connectors 104-112 to one or more of a left atrial pressure lead 122, a right ventricular pressure lead 124 and an acoustic sensor lead 126. FIG. 1 illustrates the proximal portions of the pressure leads 122, 124, while FIG. 2 illustrates the distal portions thereof. Optionally, more or fewer leads may be used, as well as different configurations of leads.

The atrial lead 116 has an atrial tip electrode 132 and an atrial ring electrode 134 implanted in the atrial appendage. The ventricular lead 118 has a ventricular tip electrode 136, a right ventricular ring electrode 138, a right ventricular coil electrode 140, and a superior vena cava (SVC) coil electrode 142. Typically, the ventricular lead 118 is transvenously inserted into the heart so as to place the RV coil electrode 140 in the right ventricular apex, and the SVC coil electrode 142 in the superior vena cava. The ventricular lead 118 is capable of receiving cardiac signals, and delivering stimulation in the form of pacing and shock therapy to the right ventricle.

The coronary sinus lead 120 is placed in the coronary sinus region via the coronary sinus for positioning a distal electrode adjacent to the left ventricle and/or additional electrode(s)

adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. The coronary sinus lead 120 may include a left ventricular tip electrode 144, a left atrial ring electrode 146, and a left atrial coil electrode 148. Optionally, the coronary sinus lead 120 may include one or more other electrodes such as the electrode 150 disposed between the LV tip electrode 144 and the LA ring electrode 146. It should also be understood that fewer or additional stimulation leads (with one or more pacing, sensing and/or shocking electrodes) may be used in order to efficiently and effectively provide pacing stimulation to the left side of the heart or atrial cardioversion and/or defibrillation.

The coronary sinus lead 120 may include a pressure sensor 152 for sensing left atrial pressure. The pressure sensor 152 enables the IMD 100 to monitor a pressure within the left atrium of the patient to obtain a physiologic index or indicator of left atrial myocardial function. The pressure sensor 152 is adapted for sensing intra-cardiac pressure as a pressure indicator that will vary over the cardiac cycle. Optionally, one or both of the right atrial lead 116 and the right ventricular lead 118 may include a pressure sensor (not shown). A pressure sensor (not shown) may be also or alternatively located in the aorta. When the pressure sensor 152 is used, one or more of the pressure leads 122, 124 may be removed entirely.

Optionally, a blood sensor 154 may be provided to measure glucose levels in the blood stream. The sensor 154 may alternatively measure natriuretic peptide levels and/or catecholamine levels in the blood stream. While sensor 154 is illustrated to be located in the right atrium, optionally, the sensor 154 may be placed in any other chamber of the heart and/or in a vein or artery outside of the heart. The sensor 154 may be placed anywhere within the circulation so long as such location experiences changes in the corresponding physiologic indices (e.g., glucose level, natriuretic peptide level, catecholamine level) at times associated with onset and termination of myocardial instability.

The IMD 100 may be coupled to the acoustic sensor 156 through the insulated conductor 158. As shown in FIG. 1, the acoustic sensor 156 is positioned proximate and external to the heart 102. Optionally, the acoustic sensor 156 may be located internal to the IMD 100 (shown as acoustic sensor 160). Optionally, an acoustic sensor 162 may be provided on one or more of the leads 116, 118, 120, 122, 124. The acoustic sensors 162 may be provided in the aorta or in any chambers of the heart from which the heart sounds are of interest. The acoustic sensors 156, 160, 162 detect heart sounds, which may represent physiologic index of myocardial function.

FIG. 2 illustrates a distal portion of the pressure leads 122, 124. The pressure leads 122, 124 may be implanted with pressure sensors 200, 202, 204. One or more pressure sensors 152 (shown in FIG. 1), 200, 202, 204 may be located in any chamber of the heart. The lead 122 includes two pressure sensors 200, 202, one of which is located in the left atrium (LA), and one of which is located in the right atrium (RA). In this embodiment, the distal tip of the lead 122 contains the left atrial pressure sensor 200. Behind the distal tip of the lead 122 is the right atrial pressure sensor 202 located on the annulus of the lead 122. As will be described below, the IMD 100 includes circuitry that processes signals from the sensors 152, 200, 202, 204 to pressures in cardiac chambers of the heart 102.

To pass the lead 122 through to the left atrium, the atrial septal wall 206 may be pierced using, for example, a piercing guide wire tool (not shown), or using a lead 122 that includes on its distal end a relatively sharp and hard tip (not shown), or using a lead that includes a deployable and retractable piercing mechanism. The piercing apparatus is manipulated to create an access tunnel 208 in the septum 206. The access tunnel 208 may be made in the region of the fossa ovalis since this may be the thinnest portion of the atrial septum 206. The distal portion of the lead 122 is then maneuvered through the atrial septum 206 (e.g., using the stylet) so that all or a portion of the pressure sensor 200 at the distal end of the lead 122 protrudes into the left atrium. The sensor 200 may be used to measure pressure in the left atrium. When the lead 122 includes pressure sensor 202 positioned proximally on the lead 122 from the sensor 200, the sensor 202 may thus be used to measure pressure in the right atrium. The lead 122 can include attachment structures 210, 212 that serve to attach the lead 122 to the septum 2. The attachment structure may take many forms including, without limitation, one or more tines, flexible membranes, inflatable membranes, circumferential tines and/or J-leads.

The pressure sensors 152 (shown in FIG. 1), 200, 202, 204 can be analog devices that produce analog signals, or digital devices that produce digital signals. Examples of an ultra small digital pressure sensor die include the SM5201 from Silicon Microstructures Incorporated (SMI) in Milpitas, Calif. An example of an ultra small analog pressure sensor die includes the SM5112 from Silicon Microstructures Incorporated (SMI) in Milpitas, Calif. It is also possible that a hollow lumen catheter can be inserted within a heart chamber, with the hollow lumen catheter being in communication with a pressure transducer located within the housing of the IMD 100. In such an embodiment, the pressure sensor is still considered to be located within a chamber of the heart since the hollow lumen can be considered part of the sensor.

The IMD 100 receives signals from one or more of the sensors 152, 154, 156, 160, 162, 200, 202, 204 (collectively referred to herein as "sensors") and the electrodes 132, 134, 136, 138, 140, 142, 144, 146, 148, 150 (collectively referred to herein as "electrodes") that measure, sense or otherwise obtain values of various physiologic indices representative of myocardial stability. In one embodiment, the physiologic indices are indicative of the same type of myocardial instability, such as heart failure. For example, the physiologic indices may represent electrical, mechanical or chemical characteristics of a patient or the patient's heart that gradually change over prolonged periods in response to heart failure. Examples of different physiologic indices or indicators that may be monitored regarding myocardial stability include electrical, mechanical, and chemical measurements. The physiologic indices may include cardiac signals such as waveforms in an IEGM or an ECG, $SvO_2$, pressure in one or more cardiac chambers of the heart 102, heart sounds, glucose level, and the like. The physiological indices represent different physiologic characteristics, each of which may undergo detectable changes during onset and/or termination of myocardial instability. Values for each of the physiological indices being monitored may be stored in a memory 608 (shown in FIG. 6) of the IMD 100. The values of the physiological indices may be recorded over multiple cardiac cycles, continuously or periodically (e.g., every hour, every day, etc.). The physiological indices may be transmitted externally to an external device 610 (shown in FIG. 6) for analysis.

Figure 3:
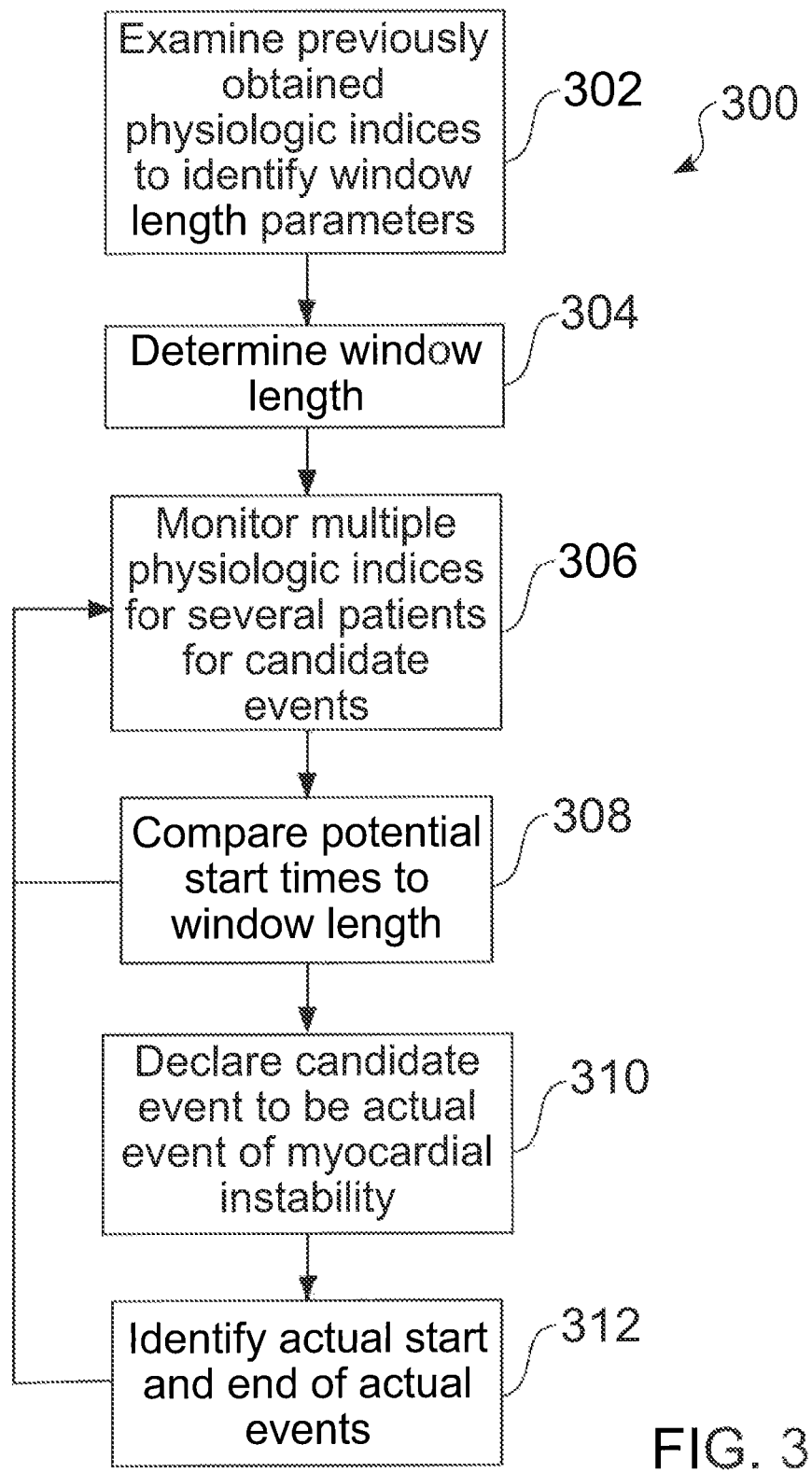
FIG. 3 is a flowchart for a process for monitoring myocardial stability that is implemented in accordance with one embodiment.

FIG. 3 is a flowchart for a process 300 for monitoring myocardial instability according to one embodiment. At 302, the method obtains pre-existing patient data that includes values measured over time for several physiologic indices of interest. The physiologic indices may be all or a subset of the physiologic indices that were previously monitored for one or more patients. For example, the physiologic indices examined at 302 may be at least two or three of the total number of physiologic indices that were previously monitored for one or more patients in a group of patients. The previously obtained physiologic indices may be obtained from a memory 608 (shown in FIG. 6) of the IMD 100 (shown in FIG. 1) from a memory such as a ROM 704, RAM 706 or hard drive 708 (shown in FIG. 7) of an external device 610 (shown in FIG. 6), from a programmer, a database, a medical network and the like. The values for the physiologic indices are examined to identify window length parameters.

At 304, a window length is determined based on the window length parameters within the pre-existing patient data. The window length represents an acceptable amount of time that may lapse between start times of predetermined variations in two or more physiologic indices and still correspond to a single common actual event. A predetermined variation represents a change in the values of a physiologic index that may be indicative of myocardial instability. For example, a predetermined variation in a physiologic index that measures myocardial pressure may indicate that the patient is exhibiting signs of heart failure. In one embodiment, a predetermined variation in a physiologic index occurs when the values of the index exceed a predetermined threshold. For example, a predetermined variation may occur when myocardial pressure measurements exceed a predetermined threshold. Alternatively, a predetermined variation in a physiologic index occurs when the values of the index fall below a predetermined threshold. For example, a predetermined variation may occur when myocardial impedance measurements fall below a predetermined threshold. In another embodiment, a predetermined variation occurs when the values of a physiologic index change by a predetermined amount. For example, a predetermined variation may occur when the measurements of a physiologic index increase or decrease by a percentage that is greater than a predetermined percentage. To better understand how a window length is determined, an example is discussed in connection with FIG. 4.

Figure 4:
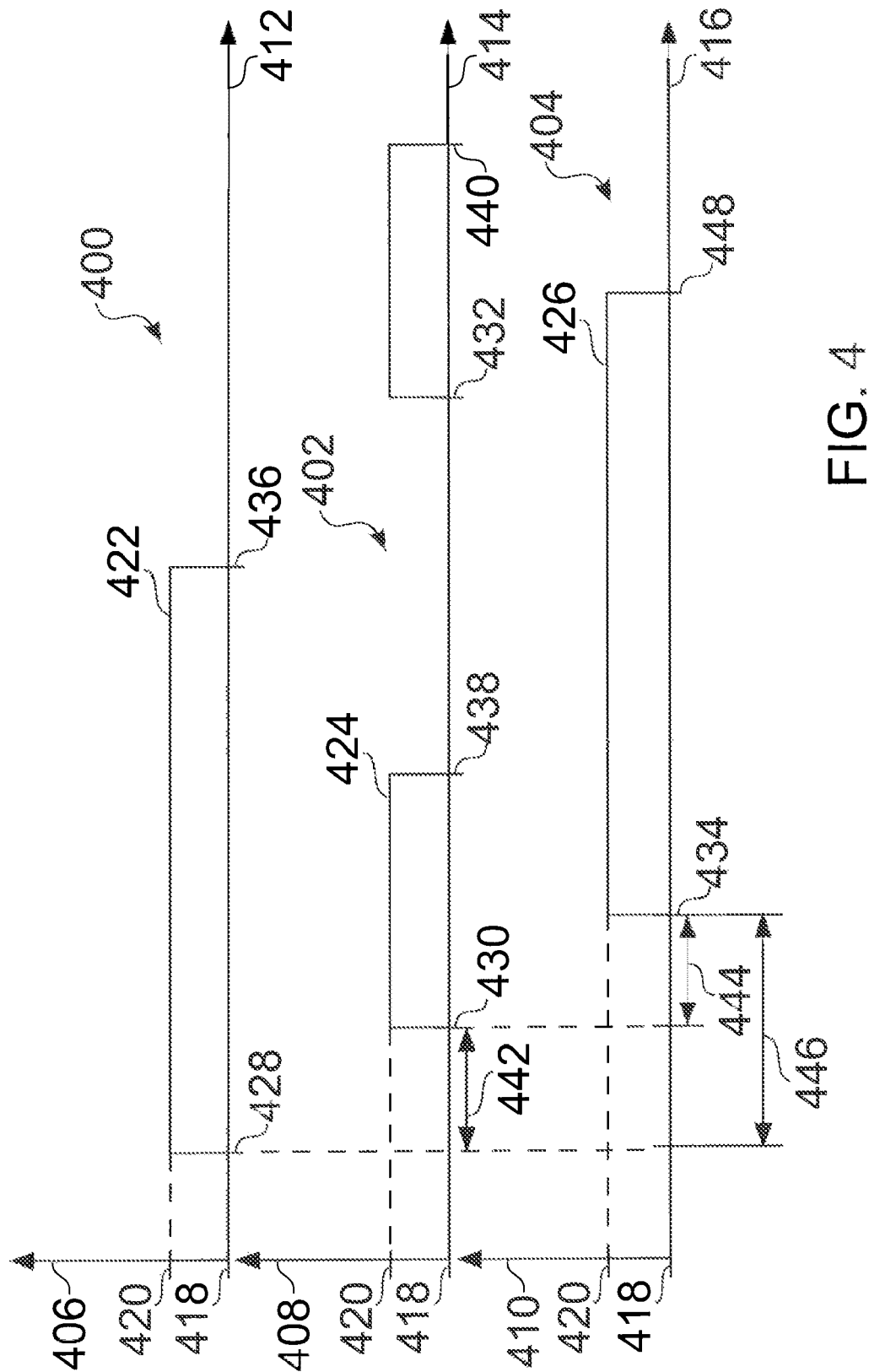
FIG. 4 illustrates an example of pre-existing patient data according to one example embodiment.

FIG. 4 illustrates an example of pre-existing patient data that may be obtained at 302. The patient data includes exemplary physiologic indices 422, 424, 426 that are plotted as graphs 400, 402, 404 with respect to time. The set of physiologic indices 422, 424, 426 shown in FIG. 4 may be associated with a known prior event of myocardial instability for a single patient. Optionally, the set of physiologic indices may be obtained from multiple patients. For example, all of the first through third physiologic indices 422-426 may be obtained for each patient in a group of patients.

A vertical axis 406, 408, 410 of each graph 400-404 represents values of the corresponding physiologic index. A horizontal axis 412, 414, 416 of each graph 400-404 represents time. The physiologic indices 422-426 varies between a baseline value 418 and an upper value 420. The baseline value 418 may represent a normalized value or range of values of each physiologic index 422-426 that is not associated with an event of myocardial instability. The upper value 420 may represent a predetermined variation in the associated physiologic index 422-426. For example, when the values of the physiologic index 422-426 do not vary by a predetermined variation, the physiologic index 422-426 maintains the baseline value 418. When the values of the physiologic index 422-426 vary by the predetermined variation, the physiologic index 422-426 shifts to the upper value 420. When a physiologic index 422-426 shifts from the baseline value 418 to the upper value 420, the change of state represents a start time for a predetermined variation. Start time 428, 430, 432, 434 are noted for predetermined variations in the physiologic indices 422-426. The graphs 400-404 corresponds to pre-existing patient data for which start and end times of known events were identified. The start times 428, 430, 432 and 434 represent the known start times at which the variation associated with a known event of myocardial instability begins. The end times 436, 438, 440, 448 represents the known end times at which the variation associated with the known event of myocardial instability ends.

In one embodiment, two of the physiologic indices 422-426 for each patient may be selected to determine the window length. For example, the first and second physiologic indices 422, 424 for each patient in a set of patients may be selected to determine the window length. The physiologic indices that are selected may be uncorrelated to one another. For example, the physiologic indices used to determine the window length may be independent of one another. Uncorrelated or independent physiologic indices may include those indices whose respective changes are not correlated or do not impact one another. For each patient, a known start time difference is calculated based on the start times 428 and 430. The known start time difference represents the amount of time that has lapsed between the known start times for each of the selected physiologic indices 422, 424. A known start time difference 442 represents the time difference between the known start times 428, 430 for the physiologic indices 422, 424 being examined. The known start time difference may be calculated for each patient in a set of patients. In one embodiment, the window length may represent the maximum known start time difference among the patients in the set of patients.

In another embodiment, all three of the physiologic indices 422-426 for each patient may be selected to determine the window length. For example, all of the physiologic indices 422-426 for each patient in a set of patients may be selected to determine the window length. Additional physiologic indices also may be used in another embodiment. For each patient, the known start time difference is calculated for each pair of physiologic indices 422-426 being examined. For example, the first known start time difference 442 is calculated for the first and second physiologic indices 422, 424. A second known start time difference 444 is calculated for the second and third physiologic indices 424, 426. A third known start time difference 446 is calculated for the first and third physiologic indices 422, 426. For each patient, the start time differences 442-446 for that patient are compared with one another to establish a patient-specific time difference. The patient-specific time difference may be the maximum of the start time differences 442-446 for that patient. For example, if the known start time differences for the first, second and third patients in the set of patients are eight, three and ten days, respectively, then the window length may be ten days. Alternatively, the window length may be calculated from a different comparison between the known start time differences. Alternatively, the patient-specific time difference may include a different comparison between the start time differences 442-446. For example, the patient-specific time difference for each patient may be the median, average, mean, minimum, and the like, of the start time differences 442-446 for that patient. The patient-specific time differences for the patients in the set of patients are then compared with one another to determine the window length. For example, the patient-specific time differences for all patients may be compared to find the largest patient-specific time difference. The window length may then represent the largest patient-specific time differences among all patients.

Returning to FIG. 3, once a window length is determined at 304, flow moves to 306. At 306, the process 300 begins to monitor multiple physiologic indices of one or more new patients for candidate events of myocardial instability. The physiologic indices that are monitored at 306 may be the same physiologic indices examined at 302. For example, the monitoring operation at 306 may be performed in real time by a bedside monitor, an implantable medical device, a programmer, an external device, and the like. The monitoring at 306 also may be conducted on newly acquired data. For example, the physiologic indices examined at 304 may be values associated with the same physiologic indices monitored at 306, but that were measured before the physiologic indices monitored at 306. The physiologic indices examined at 304 and monitored at 306 may be obtained from the same set of patients in one embodiment. For example, the physiologic indices examined at 304 may have been measured in the past while the physiologic indices examined at 306 are measured in real time. By way of example only, the physiologic indices examined at 306 may be obtained over a time period that at least partially overlaps with the time period during which the operations described in connection with the process 300 occur. In another embodiment, the physiologic indices examined at 306 were obtained during a time period occurring after the time period during which the physiologic indices examined at 304 were obtained. Alternatively, the physiologic indices may be obtained from a different set of patients. The physiologic indices monitored at 306 are examined to identify potential start and end times for candidate events of myocardial instability. Similar to the known start and end times described above, the potential start times may represent the times or dates at which physiologic indices vary by or exceed a predetermined variation and the potential end times may represent the times or dates at which the physiologic indices no longer vary by or exceed the predetermined threshold.

An event is considered a "candidate" event when i) one or more initial physiologic indices shifts from the baseline value by a predetermined variation, or the indices shift to an elevated or upper value, thereby exhibiting a potential start time and ii) a predetermined number of confirmation physiologic indices have not yet shifted to the elevated or upper values. When the initial physiologic index declares a potential event, the potential event remains a candidate event until the predetermined number of additional physiologic indices confirms the potential event or until the window length times out without confirmation. A candidate event is confirmed as an actual event when a predetermined number of physiologic events declare potential events (e.g. by shifting to the elevated value) within the window length. Conversely, a candidate event may be declared to not be an actual event when less than the predetermined number of physiologic events declare potential events within the window length.

Figure 5:
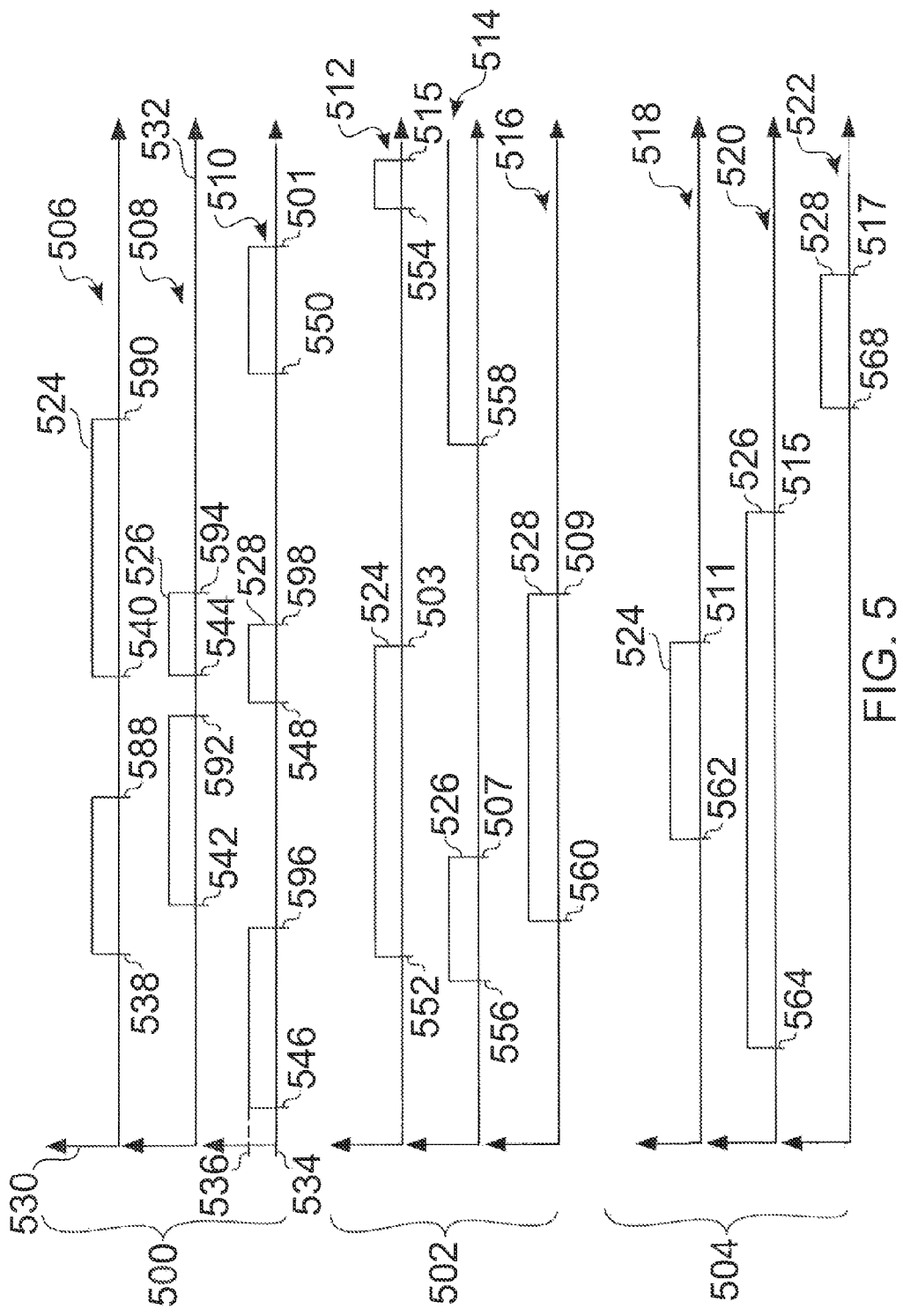
FIG. 5 is a schematic diagram of three sets of graphs illustrating exemplary values of physiologic indices that may be monitored at over time. While the patient data shown in FIG. 4 may be previously obtained data, the physiologic indices shown in FIG. 5 may be obtained in real time or during a more recent time period than the time period during which the patient data shown in FIG. 4 was obtained.

FIG. 5 is a schematic diagram of three sets 500, 502, 504 of graphs 506-522 illustrating exemplary values of physiologic indices 524, 526, 528 that may be monitored at 306 over time. In the illustrated embodiment, the first set 500 includes the physiologic indices 524-528 that were measured for a first patient, or "Patient A." The second set 502 includes the indices 524-528 measured for a second patient, or "Patient B." The third set 504 includes the indices 524-528 measured for a third patient, or "Patient C." The physiologic indices 524-528 may be uncorrelated with respect to one another. By way of example only, the first physiologic index 524 for each of Patients A, B and C may represent evoked response measurements, the second physiologic index 526 may represent variability of impedance measurements, and the third physiologic index 528 may represent $SvO_2$ measurements through each of Patient A, B and C's hearts. The second and third indices may be independent of, or uncorrelated to, the first index.

Similar to the graphs 400-404 of FIG. 4, the vertical axis 530 in each graph 506-522 represents values for the corresponding physiologic index 524-528 shown on the graph 506-522. Also similar to the graphs 400-404, the horizontal axis 532 in each graph 506-522 represents time. As with the physiologic indices shown in FIG. 4, the physiologic indices 524-528 in each set 500-504 vary between the baseline value 534 and the upper value 536. The upper values 536 of the physiologic indices 524-528 may represent candidate events of myocardial instability. In order to determine whether the candidate events are actual events of myocardial instability, potential start times 538-568 of the candidate events are identified. The potential start times 538-568 are identified by determining the times at which predetermined variations in the physiologic indices 524-528 commence. The monitoring of the physiologic indices 524-528 may involve monitoring all or a subset of the indices 524-528 in each set 500-504. For example, two of the indices 524-528 in each set 500-504 may be monitored. Alternatively, more than two indices 524-528 in each set 500-504 may be monitored. While only three physiologic indices 524-528 are in each set 500-504, a different number of indices 524-528 may be in each set 500-504. For example, a set 500-504 may include three indices. In another embodiment, a set 500-504 may include more than three indices.

At 308, the potential start times of a plurality of the physiologic indices for each patient are examined to determine if the candidate event associated with potential start times of the physiologic indices is or is not an actual event of myocardial instability. For example, at 308, the potential start times may be analyzed to determine if candidate event that is representative of heart failure is a true positive event or a false positive event. A true positive event may signify that the predetermined variations in the physiologic indices accurately represent heart failure of the patient. A false positive event may signify that the predetermined variations do not represent myocardial instability or heart failure and may be unrelated to heart failure. In one embodiment, if two physiologic indices are being monitored for each patient and the potential start times for the indices fall within the window length of one another, then, at 310, the candidate event is declared an actual event.

By way of example only, with respect to Patient A (e.g. set 500), at 308, the physiologic indices 524, 526 may be examined to determine if the first potential start times 538, 542 of the physiologic indices 524, 526 are close enough to one another to fall within the window length. If the first potential start times 538, 542 occur on January 12th and January 15th, respectively, then the potential start times 538, 542 occur within three days of one another. Similarly, with respect to Patient B (e.g. set 502), the potential start times 552, 556 are analyzed to determine if the potential start times 552, 556 fall within the window length of one another. If the potential start time 552 falls on March 10th and the potential start time 556 falls on March 9th, then the potential start times 552, 556 fall within one day of one another. If the window length was found at 304 to be tens days, then the difference between the potential start times for the first and second physiologic indices 524, 526 of Patients A and B are less than the window length. As a result, the candidate events associated with Patients A and B are declared to be actual events.

Conversely, if the potential start times for the two physiologic indices do not fall within the window length, then the candidate event is not declared an actual event. As a result, the flow of the process 300 continues back to 306. For example, with respect to Patient C (e.g. set 504), at 308, the physiologic indices 524, 526 may be examined to determine if the first potential start times 562, 564 of the physiologic indices 524, 526 are close enough to one another to fall within the window length. If the first potential start times 562, 564 occur on February 12th and February 1st, respectively, then the potential start times 562, 564 are spaced apart by eleven days. If the window length was found at 304 to be tens days, then the difference between the potential start times 562, 564 is greater than the window length. As a result, the candidate event associated with Patient C is not declared an actual event at 310.

In another embodiment, if three or more physiologic indices are being monitored for each patient, then a candidate event associated with potential start times of the physiologic indices is declared an actual event when a statistical measure of the potential start times falls within, or is no greater than, the window length. The statistical measure may represent one of the median, average, mean, maximum, minimum, and the like, of the differences between the potential start times of the physiologic indices. For example, with respect to Patient A (e.g. set 500), if the potential start times 538, 542, 546 of the physiologic indices 524-528 occur on January 12th, January 15th and January 1st, respectively, then the differences between these dates may be calculated as: three days (difference between potential start times 538 and 542), eleven days (difference between potential start times 538 and 546), and fourteen days (difference between potential start times 542 and 546). If the median, average, mean, maximum, or minimum of these differences is no greater than the window length, then, at 310, the candidate event is declared to be an actual event. For example, in one embodiment, if the mean of the date differences is compared to a window length of ten days, then the mean of three, eleven and fourteen days is found to be 9.3 days. As 9.3 days is less than the window length of ten days, the candidate event of Patient A is identified as an actual event at 310.

With respect to Patient B (e.g. set 502), the potential start times 552, 556, 560 may occur on March 10th, March 9th and March 12th. The differences between each pair of these potential start times 552, 556, 560 are one day, two days and three days. All of the median, average, mean, maximum, and minimum of these differences is less than the window length of ten days. Accordingly, the candidate event associated with Patient B is declared an actual event at 310.

Conversely, if the chosen statistical measure of the potential start times for the physiologic indices does not fall within, or is greater than, the window length, then the candidate event is not declared an actual event. For example, with respect to Patient C (e.g. set 504), the three potential start times 562, 564, 568 may occur on February 12th, February 1st and February 27th, respectively. The differences between each pair of these potential start times 562, 564, 568 are eleven days, fifteen days, and twenty-six days. If the statistical measure of the potential start times 562, 564, 568 is the median of these date differences, then the statistical measure is the median of eleven, fifteen and twenty-six. Thus, the statistical measure is fifteen days. In another example, if the statistical measure is the average of the differences between the potential start times 562, 564, 568, then the statistical measure is 17.3 days. In either example, the statistical measure of the potential start times 562, 564, 568 is greater than the window length of ten days. As a result, the candidate event associated with is not declared an actual event at 310.

At 312, one or more of the actual start and end times of the actual event of myocardial instability is identified. The actual start time may be identified as the latter of the potential start times that are associated with the actual event. For example, if the first and second physiological indices 524, 526 are monitored at 306, then the actual start time associated with the first set 500 may be the potential start time 542 of the second physiologic index 526 as the start time 542 occurs after the potential start time 538 of the first physiologic index. In another example, if three or more of the physiological indices 524-528 are monitored at 306, then the actual start time associated with the second set 502 may be the potential start time 560 of the third physiologic index 528. Alternatively, the actual start time may be the average, mean, median, first, and the like, of the potential start times associated with the actual event.

Similar to the actual start time, the actual end time may be identified as the latter of the potential end times associated with the actual event. In one embodiment, potential end times 501, 503, 505, 507, 509, 511, 515, 517, 588, 590, 592, 594, 596, 598 are identified by determining the times at which the predetermined variations in the physiologic indices 524-528 terminate. For example, if the first and second physiological indices 524, 526 are monitored at 306 and the candidate event associated with the potential start times 538, 542 is declared an actual event, then the potential end times associated with the actual event are the potential end times 588, 592. As the potential end time 592 of the second physiologic index 526 is the latter of the two potential end times 588, 592, the potential end time 592 may be identified as the actual end time at 312. In another example, if three or more of the physiological indices 524-528 are monitored at 306, then the actual end time associated with the second set 502 may be the potential end time 509 of the third physiologic index 528. Alternatively, if the actual end time may be the average, mean, median, first, and the like, of the potential end times associated with the actual event.

Figure 6:
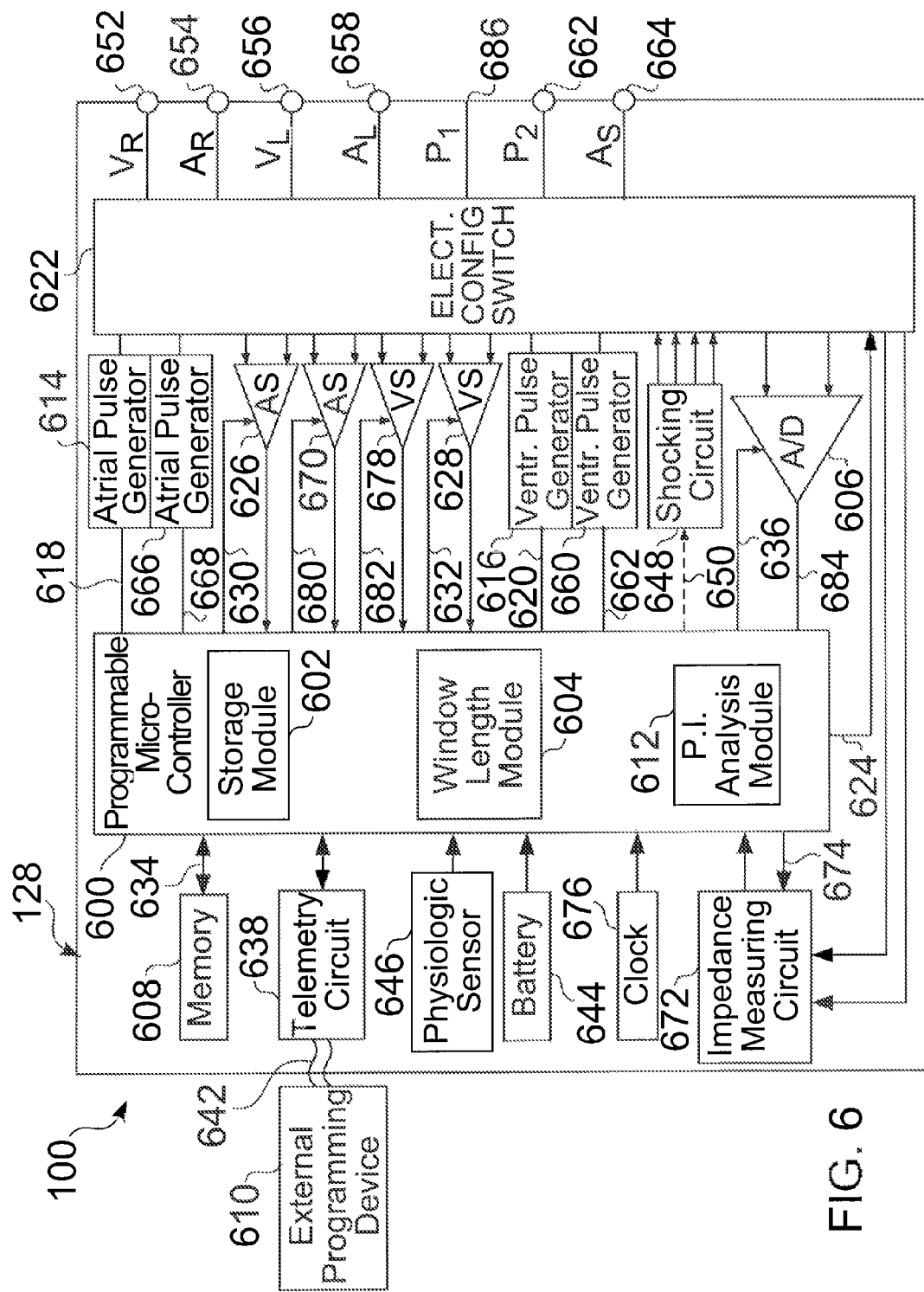
FIG. 6 illustrates a block diagram of exemplary internal components of the IMD implemented in accordance with one embodiment.

FIG. 6 illustrates a block diagram of exemplary internal components of the IMD 100. The IMD 100 is for illustration purposes only, and it is understood that the circuitry could be duplicated, eliminated, or disabled in any desired combination to provide a device capable of treating the appropriate chamber(s) of the heart with cardioversion, defibrillation, and/or pacing stimulation. As described above, the IMD 100 may be used to measure the values of multiple physiologic indices in order to permit comparison of the physiologic indices to determine if a candidate event of myocardial instability is an actual event of myocardial instability. The IMD 100 may perform one or more of the actions described above in connection with the process 300 (shown in FIG. 3).

The housing 128 for the IMD 100 is often referred to as the "can", "case", or "case electrode" and may be programmably selected to act as the return electrode for all "unipolar" pacing and defibrillation modes. The housing 128 further includes a connector (not shown) having a plurality of inputs. The inputs may include one or more of a right ventricle input terminal ($V_R$) 652, a right atrium input terminal ($A_R$) 654, a left ventricle input terminal ($V_L$) 656, a left atrium input terminal ($A_L$) 658, a first pressure sensor input terminal ($P_1$) 686, a second pressure sensor input terminal ($P_2$) 662, and an acoustic sensor input terminal ($A_S$) 664. The right ventricle input terminal 652 may be electrically coupled to the electrodes 136-142 (shown in FIG. 1), the blood sensor 154 (shown in FIG. 1) and the acoustic sensor 162 (shown in FIG. 1). Alternatively, one or more of the blood sensor 154 and the acoustic sensor 162 may be electrically coupled to a different input terminal. The right atrium input terminal 654 is electrically joined to the electrodes 132-134 (shown in FIG. 1). The left ventricle input terminal 656 is electrically connected to the electrodes 144, 150 (shown in FIG. 1). The left atrium input terminal 658 is electrically coupled to the electrodes 146, 148 (shown in FIG. 1) and the pressure sensor 152 (shown in FIG. 1). Alternatively, the pressure sensor 152 may be joined to a different input terminal. The first pressure sensor input terminal 686 is electrically connected to the pressure sensors 200, 202 (shown in FIG. 2). The second pressure sensor input terminal 662 is coupled with the pressure sensor 204 (shown in FIG. 2). Alternatively, one or more of the pressure sensors 152, 200-204 may be electrically joined with one or more different input terminals. The acoustic sensor input terminal 664 is electrically connected with the acoustic sensor 156 (shown in FIG. 1). Alternatively, the acoustic sensor 156 may be joined to one or more other input terminals. The acoustic sensor 160 (shown in FIG. 1) may be joined to one or more of the input terminals 652-664, or to an additional input terminal. The IMD 100 may include additional input terminals not illustrated in FIG. 6, such as an input terminal coupled to lead extending into the coronary sinus and joined to an electrode placed in the oblique vein of the left atrium, or the oblique vein of Marshall, to sense and pace the left atrium.

The IMD 100 includes a programmable microcontroller 600, which controls the operation of the IMD 100 based on acquired cardiac signals and obtains measurements of one or more physiologic indices. The microcontroller 600 (also referred to herein as a processor, processor module, or unit) typically includes a microprocessor, or equivalent control circuitry, and may be specifically designed for controlling the delivery of stimulation therapy and may further include RAM or ROM memory, logic and timing circuitry, state machine circuitry, and I/O circuitry. Among other things, the microcontroller 600 receives, processes, and manages storage of digitized data from one or more of the various electrodes 132-150 (shown in FIG. 1), the pressure sensors 152 (shown in FIG. 1), 200-204 (shown in FIG. 2), the blood sensor 154 (shown in FIG. 1) and the acoustic sensors 156, 160-162 (shown in FIG. 1). The microcontroller 600 may receive data from one or more additional electrodes and sensors. The data received by the microcontroller 600 includes values or signals indicative of values of the physiologic indices described above. The microcontroller 600 may include one or more modules and processors configured to perform one or more of the operations described above in connection with the process 300 and/or to enable the operations of the process 300. A storage module 602 communicates with one or more of the electrodes and sensors to direct the storage of the data or signals obtained by the electrodes and sensors in the memory 608. In one embodiment, the microcontroller 600 includes a window length module 604 that determines the window length described above. A physiologic index analysis module 612 monitors multiple ones of the physiologic indices to determine potential start and end times of candidate events of myocardial instability, as described above. Alternatively, the operations of the storage module 602, window length module 604 and/or the physiologic index analysis module 612 may be performed by a module, microcontroller or processor in the external device 610.

The microcontroller 600 may communicate with one or more of the sensors via a data signal 684 from an analog-to-digital (A/D) data acquisition system 606. The signals obtained by the sensors are applied to the inputs of the data acquisition system 606. The data acquisition system 606 converts the raw analog data of the signals into a digital signal, and communicates the digital signals as values of one or more physiologic indices to the microcontroller 600 via the data signal 684. A control signal 636 from the microcontroller 600 determines when the data acquisition system 606 acquires signals, stores the signals in the memory 608, or transmits data to the external device 610.

First and second atrial pulse generators 614, 666 and first and second ventricular pulse generators 616, 660 may generate stimulation pulses to deliver pacing therapy to the heart 102 (shown in FIG. 1). In order to provide stimulation therapy in each of the chambers of the heart 102, the atrial and ventricular pulse generators 614, 666 and 616, 660 may include dedicated, independent pulse generators, multiplexed pulse generators, or shared pulse generators. The pulse generators 614, 666 and 616, 660 are controlled by the microcontroller 600 via appropriate control signals 618, 668 and 620, 662 respectively, to trigger or inhibit the stimulation pulses.

The clock 676 is communicatively coupled to the microcontroller 600. The clock 676 measures an elapsed amount of time based on start and stop control signals from the microcontroller 600. For example, the clock 676 may begin measuring the elapsed amount of time when the microcontroller 600 sends the start signal to the clock 676. Similarly, the clock 676 may cease measuring the elapsed amount of time when the microcontroller 600 sends the stop signal to the clock 676. The time measured by the clock 676 may be stored in the memory 608 and/or communicated to the external device 610 for use in determining one or more of the window length, potential start and end times, and the actual start and end times described above.

Switch 622 includes a plurality of switches for connecting the desired electrodes, including the electrodes 132-150 (shown in FIG. 1) to the appropriate I/O circuits, thereby providing complete electrode programmability. The switch 622, in response to a control signal 624 from the microcontroller 600, determines the polarity of stimulation pulses (e.g., unipolar, bipolar, etc.) by selectively closing the appropriate combination of switches (not shown). First and second atrial sensing circuits 626, 670 and first and second ventricular sensing circuits 628, 678 also may be selectively coupled to the leads 116-120 (shown in FIG. 1) through the switch 622 for detecting the presence of cardiac activity in each of the chambers of the heart 102 (shown in FIG. 1). Control signals 630, 632, 680, 682 from microcontroller 600 direct output of the atrial and ventricular sensing circuits 626, 670 and 628, 678 that are connected to the microcontroller 600. In this manner, the atrial and ventricular sensing circuits 626, 670 and 628, 678 are able to trigger or inhibit the atrial and ventricular pulse generators 614 and 616. The switch 622 may couple the pressure sensor input terminals 686, 662 and/or the acoustic sensor input terminal 664 with the data acquisition system 606. The switch 622 may then control when the data acquisition system 606 receives signals from the sensors described above.

The memory 608 may be embodied in a computer-readable storage medium such as a ROM, RAM, flash memory, or other type of memory. The microcontroller 600 is coupled to the memory 608 by a suitable data/address bus 634, wherein the programmable operating parameters and thresholds used by the microcontroller 600 are stored and modified, as required, in order to customize the operation of IMD 100 to suit the needs of a particular patient. The memory 608 may store data indicative of the physiologic indices for a desired period of time (e.g., 6 hours, 12 hours, 18 hours or 24 hours, and the like). In one embodiment, the data indicative of the physiologic indices may be communicated to the external device 610 for analysis in accordance with one or more of the operations of the process 300.

The operating parameters of the IMD 100 may be non-invasively programmed into the memory 608 through a telemetry circuit 638 in communication with the external device 610, such as another external device, a trans-telephonic transceiver or a diagnostic system analyzer. The telemetry circuit 638 is activated by the microcontroller 600 by a control signal 640. The telemetry circuit 638 allows intra-cardiac electrograms, values of physiologic indices, time measurements, and status information relating to the operation of IMD 100 (as contained in the microcontroller 600 or memory 608), to be sent to the external device 610 through an established communication link 642. The IMD 100 additionally includes a battery 644, which provides operating power to all of the circuits shown within the housing 128, including the microcontroller 600. The IMD 100 also includes a physiologic sensor 646 that may be used to adjust pacing stimulation rate according to the exercise state of the patient. The physiologic sensor 646 also may measure or obtain one or more of the physiologic indices and communicate the indices to the microcontroller 600.

In the case where IMD 100 is intended to operate as an ICD device, the IMD 100 detects the occurrence of a shift in one or more waveforms in detected cardiac signals that indicates an arrhythmia, and automatically applies an appropriate electrical shock therapy to the heart aimed at terminating the detected arrhythmia. To this end, the microcontroller 600 further controls a shocking circuit 648 by way of a control signal 650. The shocking circuit 648 generates shocking pulses of low (up to 0.5 joules), moderate (0.5-10 joules) or high energy (11 to 40 joules). Such shocking pulses are applied to the heart 102 (shown in FIG. 1) of the patient through at least two shocking electrodes, and as shown in this embodiment, selected from the housing 128, the left atrial coil electrode 148 (shown in FIG. 1), the RV coil electrode 140 (shown in FIG. 1), and/or the SVC coil electrode 142 (shown in FIG. 1). The IMD 100 includes an impedance measuring circuit 672 enabled by the microcontroller 600 via a control signal 674. The measuring circuit 672 may be electrically coupled to the switch 622 so that impedance at any desired electrode may be obtained. The impedance measurements obtained by the impedance measuring circuit 672 may be used as one of, or as part of, the physiologic indices described above.

Figure 7:
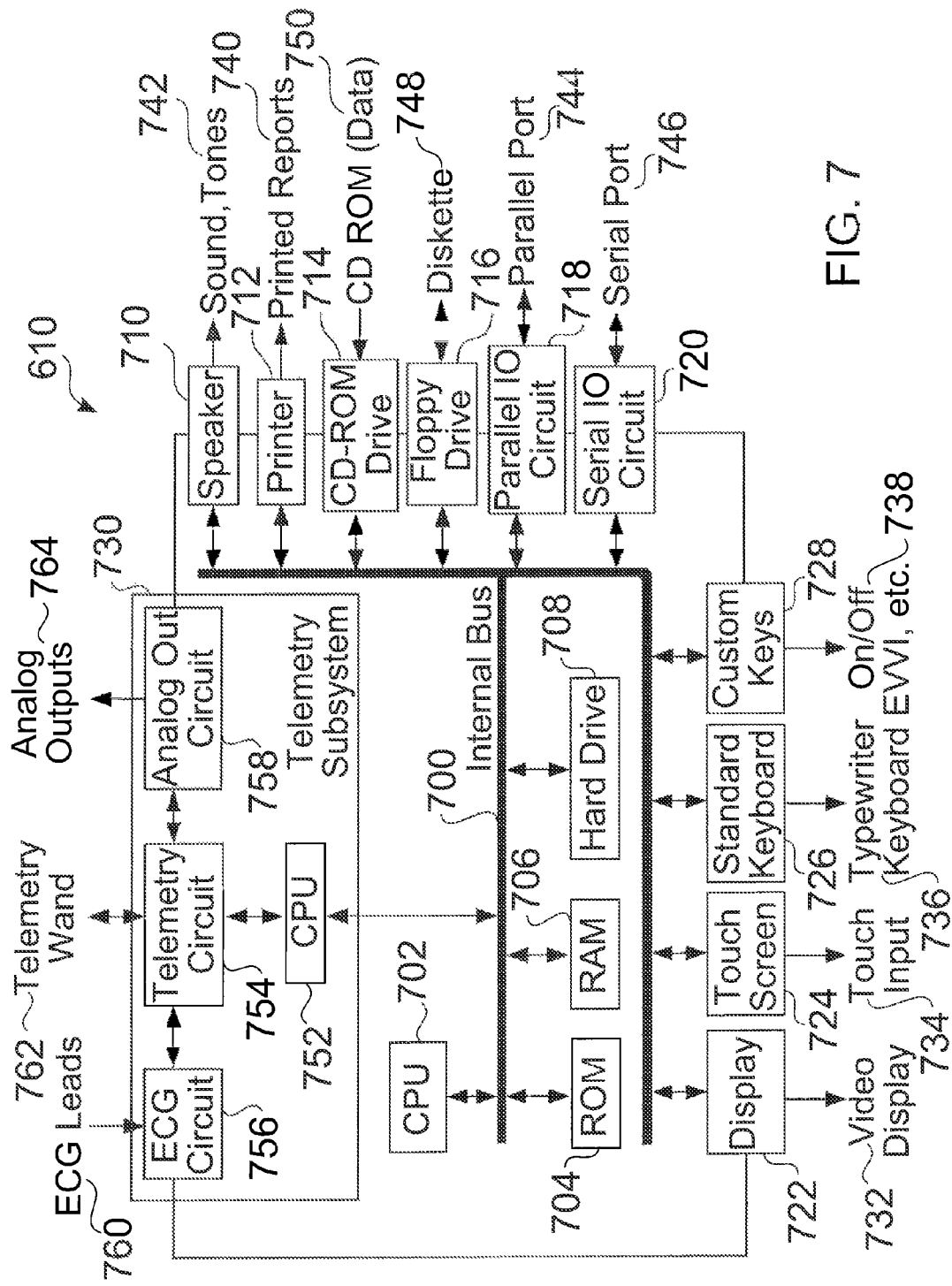
FIG. 7 illustrates a functional block diagram of an external device shown in FIG. 6 that is implemented in accordance with one embodiment.

FIG. 7 illustrates a functional block diagram of the external device 610, such as a programmer, that is operated by a physician, a health care worker, or a patient to interface with IMD 100 (shown in FIG. 1). The external device 610 may be used by a physician or operator of the IMD 100 to perform one or more of the operations of the process 300, such as determining a window length, monitoring physiologic indices for predetermined variations, potential start and end times and/or candidate events, identifying actual start and end times, and declaring actual events of myocardial instability, as described above. The external device 610 may be utilized in a hospital setting, a physician's office, or even the patient's home to communicate with the IMD 100 to change a variety of operational parameters regarding the therapy provided by the IMD 100 as well as to select among physiologic indices to be monitored and recorded by the IMD 100. For example, the external device 610 may be used to program coronary episode related parameters, such as ischemia-related and acute myocardial infarction-related ST segment shift thresholds, duration thresholds, and the like. Further, the external device 610 may be utilized to interrogate the IMD 100 to determine the condition of a patient, to adjust the physiologic indices monitored, or to adapt the therapy to a more efficacious one in a non-invasive manner. For example, the external device 610 may be used to alter one or more values or ranges of values of the predetermined variations of the physiologic indices.

The external device 610 includes an internal bus 700 that connects/interfaces with a Central Processing Unit (CPU) 702, ROM 704, RAM 706, hard drive 708, the speaker 710, a printer 712, a CD-ROM drive 714, a floppy drive 716, a parallel I/O circuit 718, a serial I/O circuit 720, the display 722, a touch screen 724, a standard keyboard connection 726, custom keys 728, and a telemetry subsystem 730. The internal bus 700 is an address/data bus that transfers information (e.g., either memory data or a memory address from which data will be either stored or retrieved) between the various components described herein. The hard drive 708 may store operational programs as well as data, such as the values of physiologic indices for multiple patients, potential start and end times, actual start and end times, candidate and actual events, the limits of the predetermined variations, and the like.

The CPU 702 typically includes a microprocessor, a microcontroller, or equivalent control circuitry, designed specifically to control interfacing with the external device 610 and with the IMD 100. The CPU 702 may include one or more of the modules described above in connection with the microcontroller 600 (shown in FIG. 6) of the IMD 100 (shown in FIG. 1). For example, the CPU 702 may include the storage module 602 for directing the storage of physiologic indices, potential and actual start and end times, candidate and actual events, predetermined variations, and the like. The CPU 702 may include the window length module for determining the window length and the physiologic index analysis module 612 for monitoring physiologic indices for multiple patients and determining which of candidate events are actual events of myocardial instability, as described above. The CPU 702 may further include RAM or ROM memory, logic and timing circuitry, state machine circuitry, and I/O circuitry to interface with the IMD 100. Typically, the microcontroller 600 includes the ability to process or monitor input signals (e.g., data) as controlled by program code stored in memory (e.g., ROM 704).

The display 722 (e.g., may be connected to the video display 732) and the touch screen 724 display text, alphanumeric information, data and graphic information via a series of menu choices to be selected by the user relating to the IMD 100 (shown in FIG. 1), such as for example, status information, operating parameters, therapy parameters, patient status, access settings, software programming version, physiologic indices, predetermined variations, actual and potential start and end times, actual and candidate events, and the like. The touch screen 724 accepts a user's touch input 734 when selections are made. The keyboard 726 (e.g., a typewriter keyboard 736) allows the user to enter data to the displayed fields, operational parameters, therapy parameters, as well as interface with the telemetry subsystem 730. Furthermore, custom keys 728 turn on/off 738 (e.g., EVVI) the external device 610.

The printer 712 prints copies of reports 740 for a physician to review or to be placed in a patient file, and speaker 710 provides an audible warning (e.g., sounds and tones 742) to the user in the event of a potential deleterious programming value or if a patient has any abnormal physiological condition occur while the external device 610 is being used. The parallel I/O circuit 718 interfaces with a parallel port 744. The serial I/O circuit 720 interfaces with a serial port 746. The floppy drive 716 accepts diskettes 748. Optionally, the floppy drive 716 may include a USB port or other interface capable of communicating with a USB device such as a memory stick. The CD-ROM drive 714 accepts CD ROMs 750.

The telemetry subsystem 730 includes a central processing unit (CPU) 752 in electrical communication with a telemetry circuit 754, which communicates with both an ECG circuit 756 and an analog out circuit 758. The ECG circuit 756 is connected to ECG leads 760. The telemetry circuit 754 is connected to a telemetry wand 762. The analog out circuit 758 includes communication circuits, such as a transmitting antenna, modulation and demodulation stages (not shown), as well as transmitting and receiving stages (not shown) to communicate with analog outputs 764. The external device 610 may wirelessly communicate with the IMD 100 (shown in FIG. 1) and utilize protocols, such as Bluetooth, GSM, infrared wireless LANs, HIPERLAN, 3G, satellite, as well as circuit and packet data protocols, and the like. A wireless RF link utilizes a carrier signal that is selected to be safe for physiologic transmission through a human being and is below the frequencies associated with wireless radio frequency transmission. Alternatively, a hard-wired connection may be used to connect the external device 610 to IMD 100 (e.g., an electrical cable having a USB connection).

Figure 8:
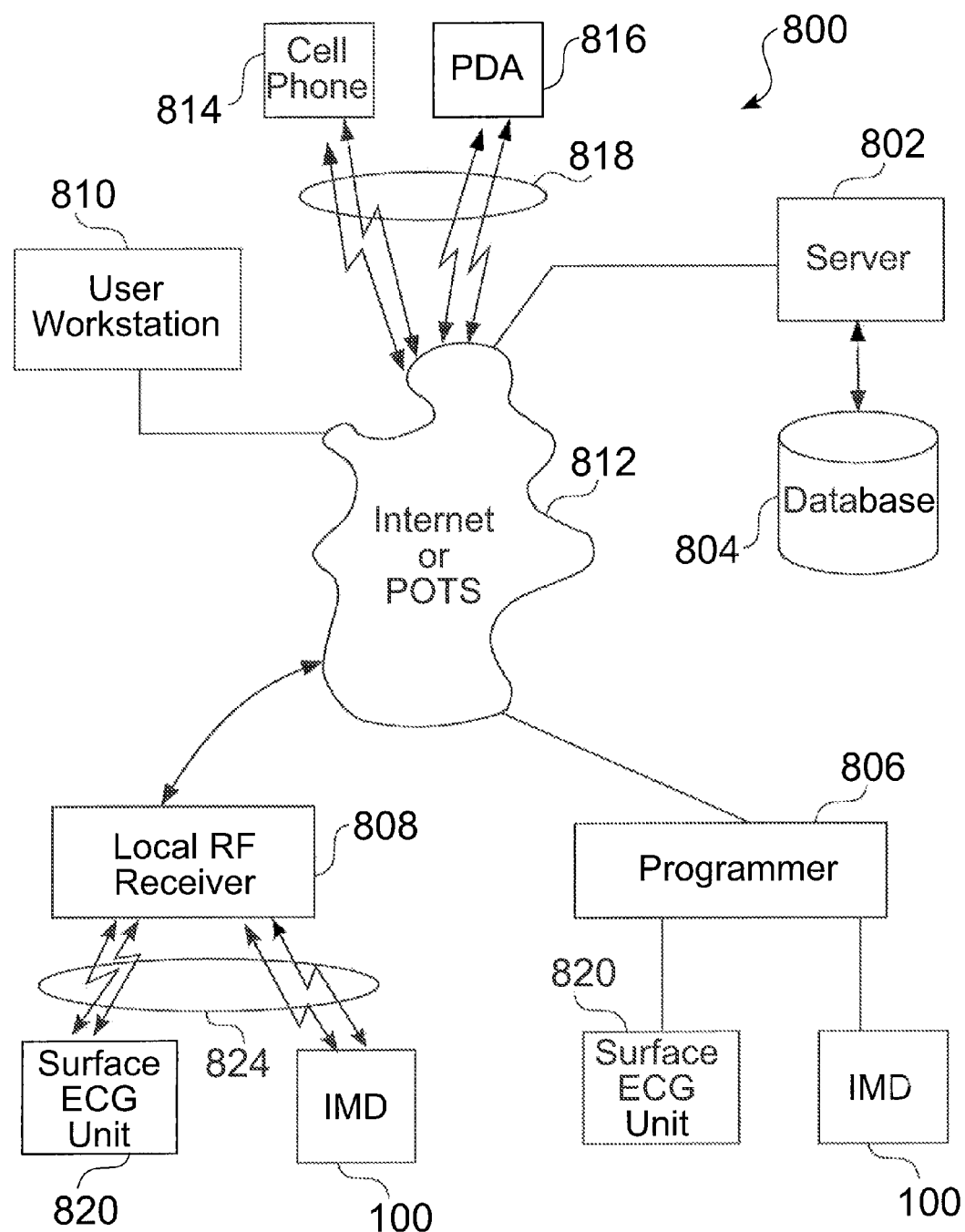
FIG. 8 illustrates a distributed processing system that is implemented in accordance with one embodiment.

FIG. 8 illustrates a distributed processing system 800 in accordance with one embodiment. The distributed processing system 800 includes a server 802 that is connected to a database 804, a programmer 806 (e.g., similar to external device 610 described above and shown in FIG. 6), a local RF transceiver 808 and a user workstation 810 electrically connected to a communication system 812. The communication system 812 may be the internet, a voice over IP (VoIP) gateway, a local plain old telephone service (POTS) such as a public switched telephone network (PSTN), a cellular phone based network, and the like. Alternatively, the communication system 812 may be a local area network (LAN), a campus area network (CAN), a metropolitan area network (MAN), or a wide area network (WAM). The communication system 812 serves to provide a network that facilitates the transfer/receipt of physiologic indices, predetermined variations, window lengths, actual and potential start and end times, candidate and actual events, and the like.

The server 802 is a computer system that provides services to other computing systems (e.g., clients) over a computer network. The server 802 acts to control the transmission and reception of information (e.g., physiologic indices, predetermined variations, window lengths, actual and potential start and end times, candidate and actual events, and the like). The server 802 interfaces with the communication system 812 to transfer information between the programmer 806, the local RF transceiver 808, the user workstation 810 as well as a cell phone 814, and a personal data assistant (PDA) 816 to the database 804 for storage/retrieval of records of information. For instance, the server 802 may download, via a wireless connection 818, to the cell phone 814 or the PDA 816, physiologic indices, predetermined variations, window lengths, actual and potential start and end times, candidate and actual events, and the like. On the other hand, the server 802 may upload raw cardiac signals (e.g., unprocessed cardiac data) from a surface ECG unit 820 or the IMD 100 via the local RF transceiver 808 or the programmer 806.

Database 804 is any commercially available database that stores information in a record format in electronic memory. The database 804 stores information such as the values of physiologic indices, predetermined variations, window lengths, actual and potential start and end times, candidate and actual events, and the like, for multiple patients. The information is downloaded into the database 804 via the server 802 or, alternatively, the information is uploaded to the server from the database 804.

The programmer 806 is similar to the external device 610 (shown in FIG. 6) and may reside in a patient's home, a hospital, or a physician's office. Programmer 806 interfaces with the surface ECG unit 820 and the IMD 100. The programmer 806 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the programmer 806 to the IMD 100. The programmer 806 is able to acquire cardiac signals from the surface of a person (e.g., ECGs), intra-cardiac electrogram (e.g., IEGM) signals from the IMD 100, and/or values of physiologic indices from the IMD 100. The programmer 806 interfaces with the communication system 812, either via the internet or via POTS, to upload the cardiac data acquired from the surface ECG unit 820 or the IMD 100 to the server 802. The programmer 806 may upload values or ranges for the predetermined variations, values of physiologic indices, status information, operating parameters, therapy parameters, patient status, access settings, software programming version, and the like.

The local RF transceiver 808 interfaces with the communication system 812, via a communication link 824, to upload values of physiologic indices acquired from the surface ECG unit 820 or the IMD 100 to the server 802. In one embodiment, the surface ECG unit 820 and the IMD 100 have a bidirectional connection with the local RF transceiver via a wireless connection. The local RF transceiver 808 is able to acquire cardiac signals from the surface of a person (e.g., ECGs), intra-cardiac electrogram (e.g., IEGM) signals from the IMD 100, and/or the values of physiologic indices from the IMD 100. On the other hand, the local RF transceiver 808 may download stored physiologic indices, predetermined variations, window lengths, actual and potential start and end times, candidate and actual events, and the like, cardiac data from the database 804 to the surface ECG unit 820 or the IMD 100.

The user workstation 810 may interface with the communication system 812 via the internet or POTS to download values of the physiologic indices via the server 802 from the database 804. Alternatively, the user workstation 810 may download raw data from the surface ECG unit 820 or IMD 100 via either the programmer 806 or the local RF transceiver 808. Once the user workstation 810 has downloaded the physiologic indices, the user workstation 810 may process the information in accordance with one or more of the operations described above in connection with the process 300. For example, the user workstation 810 may determine window lengths, monitor physiologic indices for multiple patients, identify candidate events and associated potential start and end times, and declare actual events and associated actual start and end times. The user workstation 810 may be used to adjust the predetermined variations. For example, the user workstation 810 may alter the thresholds or variations from a threshold that are used to determine whether one or more of the physiologic indices has varied by a predetermined variation. The user workstation 810 may download the information to the cell phone 816, the PDA 818, the local RF transceiver 808, the programmer 806, or to the server 802 to be stored on the database 804.

Figure 9:
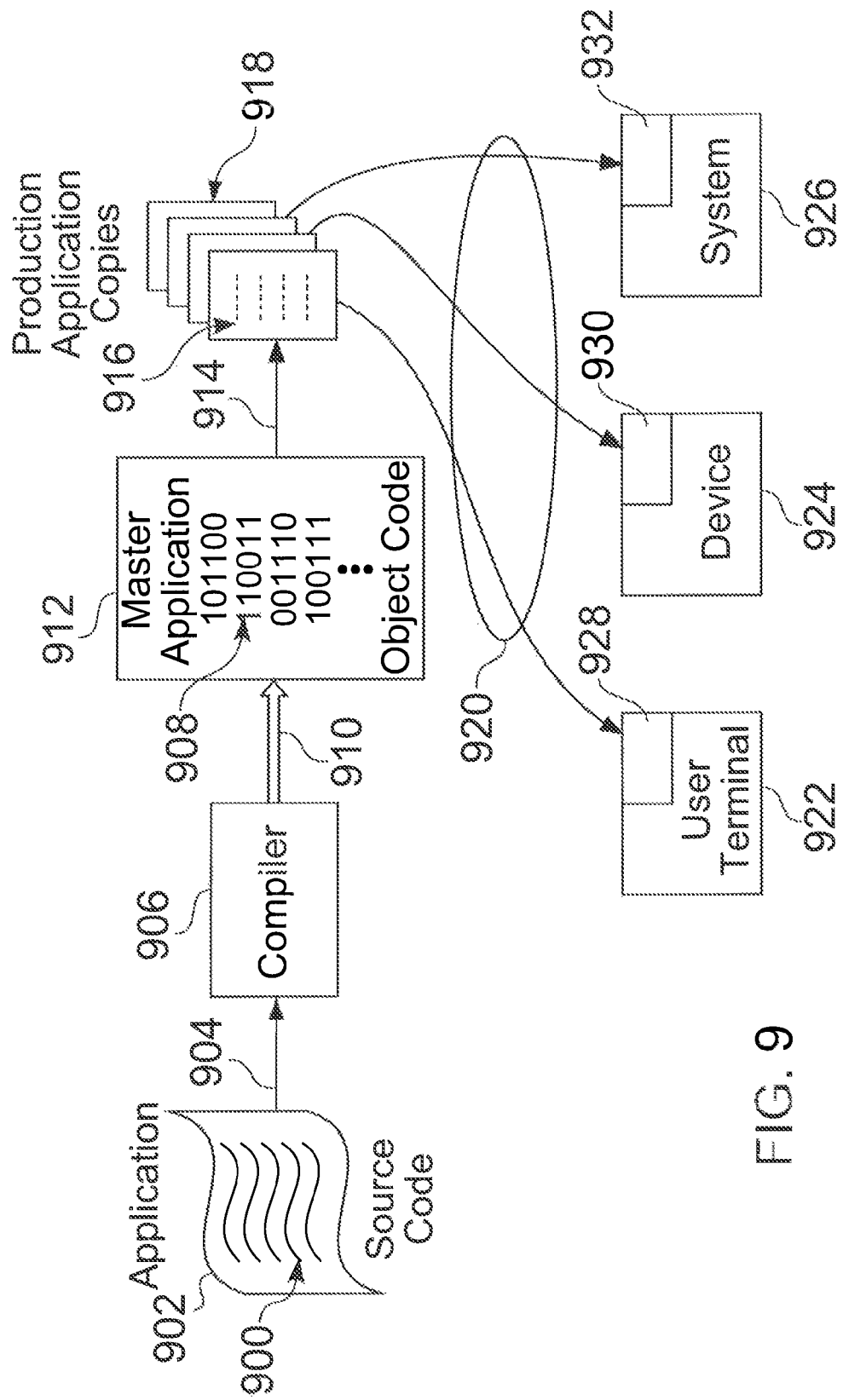
FIG. 9 illustrates a block diagram of exemplary manners in which embodiments of the present invention may be stored, distributed, and installed on a computer-readable medium.

FIG. 9 illustrates a block diagram of exemplary manners in which embodiments of the present invention may be stored, distributed, and installed on a computer-readable medium. In FIG. 9, the "application" represents one or more of the methods and process operations discussed above. For example, the application may represent the processes carried out in connection with FIGS. 1 through 8 as discussed above. As shown in FIG. 9, the application is initially generated and stored as source code 900 on a source computer-readable medium 902. The source code 900 is then conveyed over path 904 and processed by a compiler 906 to produce object code 908. The object code 908 is conveyed over path 910 and saved as one or more application masters on a master computer-readable medium 912. The object code 908 is then copied numerous times, as denoted by path 914, to produce production application copies 916 that are saved on separate production computer-readable medium 918. The production computer-readable medium 918 is then conveyed, as denoted by path 920, to various systems, devices, terminals and the like. In the example of FIG. 9, a user terminal 922, a device 924 and a system 926 are shown as examples of hardware components, on which the production computer-readable medium 918 are installed as applications (as denoted by 928 through 932). For example, the production computer-readable medium 918 may be installed on the IMD 100 (shown in FIG. 1) and/or the microcontroller 600 (shown in FIG. 6).

The source code may be written as scripts, or in any high-level or low-level language. Examples of the source, master, and production computer-readable medium 902, 912, and 918 include, but are not limited to, CDROM, RAM, ROM, Flash memory, RAID drives, memory on a computer system, and the like. Examples of the paths 904, 910, 914, and 920 include, but are not limited to, network paths, the internet, Bluetooth, GSM, infrared wireless LANs, HIPERLAN, 3G, satellite, and the like. The paths 904, 910, 914, and 920 may also represent public or private carrier services that transport one or more physical copies of the source, master, or production computer-readable medium 902, 912 or 918 between two geographic locations. The paths 904, 910, 914 and 920 may represent threads carried out by one or more processors in parallel. For example, one computer may hold the source code 900, compiler 906 and object code 908. Multiple computers may operate in parallel to produce the production application copies 916. The paths 904, 910, 914, and 920 may be intra-state, inter-state, intra-country, inter-country, intra-continental, inter-continental, and the like.

The operations noted in FIG. 9 may be performed in a widely distributed manner world-wide with only a portion thereof being performed in the United States. For example, the application source code 900 may be written in the United States and saved on a source computer-readable medium 902 in the United States, but transported to another country (corresponding to path 904) before compiling, copying and installation. Alternatively, the application source code 900 may be written in or outside of the United States, compiled at a compiler 906 located in the United States and saved on a master computer-readable medium 912 in the United States, but the object code 908 transported to another country (corresponding to path 914) before copying and installation. Alternatively, the application source code 900 and object code 908 may be produced in or outside of the United States, but production application copies 916 produced in or conveyed to the United States (for example, as part of a staging operation) before the production application copies 916 are installed on user terminals 922, devices 924, and/or systems 926 located in or outside the United States as applications 928 through 932.

As used throughout the specification and claims, the phrases "computer-readable medium" and "instructions configured to" shall refer to any one or all of (i) the source computer-readable medium 902 and source code 900, (ii) the master computer-readable medium and object code 908, (iii) the production computer-readable medium 918 and production application copies 916 and/or (iv) the applications 928 through 932 saved in memory in the terminal 922, device 924, and system 926.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of monitoring myocardial stability comprising:
    determining a window length representing an acceptable maximum time period corresponding to a single common actual event of myocardial instability between potential start times associated with at least two physiologic indices representative of myocardial stability;
    monitoring multiple physiologic indices using sensors, the physiologic indices being representative of myocardial stability, wherein predetermined variations in each of the physiologic indices denote the potential start times and potential end times for candidate events indicative of myocardial instability;
    identifying the potential start times associated with at least two of the monitored physiologic indices; and
    declaring at least one of the candidate events to be an actual event of myocardial instability based on the window length and a time period between the potential start times identified by the identifying operation.

2. The method of claim 1, wherein the physiologic indices used to determine window length, are uncorrelated with respect to one another.

3. The method of claim 1, further comprising:
    identifying a known prior event of myocardial instability and known start times for multiple physiologic indices corresponding to the known prior event; and
    deriving the window length based on a time period between the known start times corresponding to the known prior event.

4. The method of claim 1, further comprising, for multiple patients:

identifying, for each patient, a known prior event and known start times for multiple physiologic indices corresponding to the known prior event; and deriving the window length based on a time period between the known start times for the multiple patients.

5. The method of claim 1, further comprising determining an event start time at which the actual event commences based on the potential start times identified by the identifying operation.

6. The method of claim 1, wherein the identifying operation comprises identifying the potential end times associated with at least two of the monitored physiologic indices, further comprising determining an event end time at which the actual event terminates based on the potential end times identified by the identifying operation.

7. The method of claim 1, wherein the potential start times are identified when values of at least one of the physiologic indices exceeds an associated threshold.

8. The method of claim 1, wherein the potential end times are identified when values of at least one of the physiologic indices falls below an associated threshold.

9. The method of claim 1, wherein the declaring operation declares the candidate event to be the actual event when the time period between the potential start times is no greater than the window length.

10. A non-transitory computer readable storage medium for a computing device having a memory and a microcontroller, the computer readable storage medium comprising instructions to:
    direct the memory to store values of multiple physiologic indices indicative of myocardial stability; and
    direct the microcontroller to:
        determine a window length representing an acceptable maximum time period corresponding to a single common actual event of myocardial instability between potential start times associated with at least two of the physiologic indices;
        monitor multiple physiologic indices, wherein predetermined variations in each of the physiologic indices denote the potential start times and potential end times for candidate events indicative of myocardial instability;
        identify the potential start times associated with at least two of the monitored physiologic indices; and
        declare at least one of the candidate events to be an actual event of myocardial instability based on the window length and a time period between the potential start times identified by the microcontroller.

11. The computer readable storage medium of claim 10, wherein the monitored physiologic indices are uncorrelated with respect to one another.

12. The computer readable storage medium of claim 10, further comprising instructions to direct the microcontroller to:
    identify a known prior event of myocardial instability and known start times for multiple physiologic indices corresponding to the known prior event; and
    derive the window length based on a time period between the known start times corresponding to the known prior event.

13. The computer readable storage medium of claim 10, further comprising instructions:
    to direct the memory to store values of multiple physiologic indices indicative of myocardial stability for each of multiple patients; and
    to direct the microcontroller to:
        identify, for each patient, a known prior event and known start times for multiple physiologic indices corresponding to the known prior event; and
        derive the window length based on a time period between the known start times for the multiple patients.

14. The computer readable storage medium of claim 10, further comprising instructions to direct the microcontroller to determine an event start time at which the actual event commences based on the identified potential start times.

15. The computer readable storage medium of claim 10, wherein the instructions direct the microcontroller to identify the potential end times associated with at least two of the monitored physiologic indices and determine an event end time at which the actual event terminates based on the potential end times identified by the microcontroller.

16. The computer readable storage medium of claim 10, wherein the instructions direct the microcontroller to identify the potential start times when values of at least one of the physiologic indices exceed an associated threshold.

17. The computer readable storage medium of claim 10, wherein the instructions direct the microcontroller to identify the potential end times when values of at least one of the physiologic indices falls below an associated threshold.

18. The computer readable storage medium of claim 10, wherein the instructions direct the microcontroller to declare the candidate event to be the actual event when the time period between the potential start times is no greater than the window length.

19. A system for monitoring myocardial stability comprising:
    sensors configured to obtain values of multiple physiologic indices representative of myocardial stability; and
    a computing device for examining the physiologic indices to determine whether predetermined variations in the physiologic indices represent myocardial instability by:
        determining a window length indicative of an acceptable maximum time period corresponding to a single common actual event of myocardial instability between potential start times associated with at least two physiologic indices;
        monitoring multiple physiologic indices representative of myocardial instability for predetermined variations indicative of the potential start times and potential end times for candidate events representative of myocardial instability;
        identifying the potential start times associated with at least two of the monitored physiologic indices; and
        declaring at least one of the candidate events to be an actual event of myocardial instability based on the window length and a time period between the potential start times identified by the identifying operation.

20. The system of claim 19, wherein the computing device is configured to identify a known prior event of myocardial instability and known start times for multiple physiologic indices corresponding to the known prior event, and to derive the window length based on a time period between the known start times corresponding to the known prior event.

21. The system of claim 19, further comprising a memory for storing the values of multiple physiologic indices for multiple patients, wherein the computing device identifies, for each patient, a known prior event and known start times for multiple physiologic indices corresponding to the known prior event and derives the window length based on a time period between the known start times for the multiple patients.

22. The system of claim 19, wherein the computing device determines an event start time at which the actual event commences based on the potential start times identified by the computing device.

23. The system of claim 19, wherein the computing device is configured to identify the potential end times associated with at least two of the monitored physiologic indices and determine an event end time at which the actual event terminates based on the potential end times identified by the computing device.

24. The system of claim 19, wherein the computing device identifies the potential start times when values of at least one of the physiologic indices exceeds an associated threshold.

25. The system of claim 19, wherein the computing device declares the candidate event to be the actual event when the time period between the potential start times is no greater than the window length.

* * * * *